(12) United States Patent
Peglion et al.

(10) Patent No.: US 7,470,683 B2
(45) Date of Patent: Dec. 30, 2008

(54) TETRACYCLIC COMPOUNDS

(75) Inventors: Jean-Louis Peglion, Le Vesinet (FR); Christophe Poitevin, Paris (FR); Mark Millan, Le Pecq (FR); Mauricette Brocco, Paris (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 0 days.

(21) Appl. No.: 11/904,006

(22) Filed: Sep. 25, 2007

(65) Prior Publication Data

US 2008/0076765 A1    Mar. 27, 2008

(30) Foreign Application Priority Data

Sep. 26, 2006 (FR) .................................. 06 08413

(51) Int. Cl.
*C07D 498/04* (2006.01)
*A61K 31/53* (2006.01)

(52) U.S. Cl. ...................... 514/229.8; 544/99
(58) Field of Classification Search ................. 544/99; 514/229.8

See application file for complete search history.

(56) References Cited

FOREIGN PATENT DOCUMENTS

| EP | 0080115 | 6/1983 |
|---|---|---|
| EP | 0686637 | 12/1995 |
| EP | 0773223 | 5/1997 |
| EP | 0899267 | 3/1999 |

OTHER PUBLICATIONS

Peglion, et al., "Tetracyclic analogs of [+]-S 14297: synthesis and determination of affinity and selectivity at cloned human dopamine D3 vs. D2 receptors" Bioorganic & Mecidinal Chemistry Letters, 7(7), 881-886, 1997.
French Preliminary Search Report for FR0608413 of Apr. 18, 2007.

*Primary Examiner*—Kahsay T Habte
(74) *Attorney, Agent, or Firm*—Hueschen and Sage

(57) ABSTRACT

Compounds of formula I, of trans relative configuration:

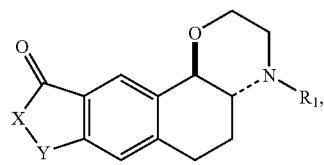

I wherein:
X represents an oxygen atom or an $NR_2$ group,
Y represents a group selected from $—CH_2—$, $—(CH_2)_2—$ and $—CH=CH—$,
$R_1$ and $R_2$, which may be the same or different, each represents a hydrogen atom or a group selected from alkyl, cycloalkyl and cycloalkylalkyl,
in racemic form or in the form of optical isomers,
and also addition salts thereof with a pharmaceutically acceptable acid, and hydrates thereof.

Medicinal products containing the same which are useful in the treatment of disorders of the central nervous system that involve the dopaminergic system.

7 Claims, No Drawings

TETRACYCLIC COMPOUNDS

The present invention relates to new tetracyclic compounds, to a process for their preparation and to pharmaceutical compositions containing them.

More specifically, the invention relates to compounds of formula I, of trans relative configuration:

wherein:
- X represents an oxygen atom or an $NR_2$ group,
- Y represents a group selected from $-CH_2-$, $-(CH_2)_2-$ and $-CH=CH-$,
- $R_1$ and $R_2$, which may be the same or different, each represents a hydrogen atom or a group selected from linear or branched $C_1-C_6$alkyl, $C_3-C_8$cycloalkyl, and cycloalkylalkyl wherein the alkyl moiety is $C_1-C_6$ and is linear or branched and the cycloalkyl moiety is $C_3-C_8$, in racemic form or in the form of optical isomers, and also to addition salts thereof with a pharmaceutically acceptable acid, and hydrates thereof.

A $C_3-C_8$cycloalkyl group is understood to be a 3- to 8-membered monocyclic saturated hydrocarbon group.

Among the pharmaceutically acceptable acids there may be mentioned by way of non-limiting example hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid, camphoric acid and dibenzoyltartaric acid.

One aspect of the present invention relates to compounds of formula I wherein $R_1$ represents an alkyl group, especially a propyl group.

Another aspect of the present invention relates to compounds of formula I wherein X represents an $NR_2$ group, especially an NH group.

Another aspect of the present invention relates to compounds of formula I wherein Y represents a $CH_2$ group.

Another aspect of the present invention relates to the following compounds of formula I:
- (4aRS,11bRS)-4-propyl-3,4,4a,5,6,8,9,11b-octahydroisoindolo[5,6-h][1,4]benzoxazin-10(2H)-one, and also its enantiomers, and addition salts thereof with a pharmaceutically acceptable acid;
- (4aR,11bR)-4-propyl-2,3,4,4a,5,6,8,11b-octahydro-10H-furo[3',4':6,7]naphtho-[1,2-b][1,4]oxazin-10-one, and also addition salts thereof with a pharmaceutically acceptable acid;
- (4aR,12bR)-4-propyl-3,4,4a,5,6,8,9,12b-octahydro-2H,11H-pyrano[4',3':6,7]naphtho-[1,2-b][1,4]oxazin-11-one, and also addition salts thereof with a pharmaceutically acceptable acid;
- (4aR,12bR)-4-propyl-2,3,4,4a,5,6,8,9,10,12b-decahydro-11H-isoquino[6,7-h][1,4]benzoxazin-11-one, and also addition salts thereof with a pharmaceutically acceptable acid; and
- (4aR,12bR)-4-propyl-2,3,4,4a,5,6,10,12b-octahydro-11H-isoquino[6,7-h][1,4]benzoxazin-11-one, and also addition salts thereof with a pharmaceutically acceptable acid.

The compounds of formula I act as powerful dopaminergic ligands.

Dopaminergic compounds are widely used in therapy by virtue of their beneficial effects in psychiatric and neurological disorders and, peripherally, in cardiovascular disorders.

Five dopaminergic receptor sub-types ($D_1$ to $D_5$) have been cloned and characterised to date. The great majority of medicaments in this class currently act on the dopaminergic system by means of their action on the $D_2$ sub-type, either as blockers (or antagonists) or as activators (or agonists). These medicaments have numerous secondary effects: dyskinesia, hyperprolactinaemia and amenorrhoea in the case of the former and cardiovascular and emetic effects in the case of the latter.

In contrast to $D_2$ receptors, the concentration of $D_3$ receptors is very low in the nigrostriatal nucleus and in lactotroph cells (Pharmacol Ther. 2001, 90(2-3), 231-59; CNS Neurol Disord Drug Targets 2006, 5(1), 25-43). On the other hand, similarly to $D_2$ receptors, the concentration of $D_3$ receptors is very high in the limbic system (Pharmacol Ther. 2001, 90(2-3), 231-59; CNS Neurol Disord Drug Targets 2006, 5(1), 25-43). This significant difference in the location of these two receptor sub-types is prompting the search for new medicaments that act preferentially on the $D_3$ sub-type, which should be accompanied by minimisation of the secondary effects typically associated with the $D_2$ sub-type as mentioned hereinbefore (Pharmacol Ther. 2001, 90(2-3), 231-59; J Pharmacol Exp Ther. 2004, 309(3), 936-50; J Pharmacol Exp Ther. 2004, 309(3), 921-35; CNS Neurol Disord Drug Targets 2006, 5(1), 25-43).

Di-substituted trans-3,4,4a,5,6,10b-hexahydro-2H-naphth[1,2-b]-1,4-oxazines have been described as dopaminergic ligands in the patent specification EP 0 899 267.

The compounds of the present invention behave as preferential ligands of $D_3$ receptors, with a lesser affinity for the $D_2$ receptor.

This characteristic makes the compounds of the present invention especially valuable by virtue of the fact that they exhibit a low level of secondary effects.

A number of tests have confirmed their mechanism of action and the value of their use in the treatment of numerous disorders of the central nervous system.

In particular, the compounds of the invention exhibit their activity in the presynaptic dopaminergic autoreceptor activation test, in the forced swimming test, in the ultrasonic vocalisation test, and in the rotation test on 6-OH-DA-lesioned rats.

These results allow the products of the invention to be proposed for neuroprotection and for the treatment of disorders of the central nervous system that involve the dopaminergic system, such as Parkinson's disease (Pharmacol Ther. 2001, 90(2-3), 231-59; J Pharmacol Exp Ther. 2004, 309(3), 936-50; CNS Neurol Disord Drug Targets 2006, 5(1), 25-43), hyperprolactinaemia (Pharmacol Ther. 2001, 90(2-3), 231-59; Curr Opin Obstet Gynecol. 1993, 5(3), 360-7), sexual dysfunction (Physiol Behav. 2004, Vol 83, 291-307; J. Neurosci. 1999, Vol 19, 456-463), depression (Pharmacol Ther. 2006, 110(2), 135-370; J Pharmacol Exp Ther. 2004, 309(3), 936-50), anxiety (Prog Neurobiol. 2003, 70(2), 83-244; J Pharmacol Exp Ther. 2004, 309(3), 936-50), Alzheimer's disease and other neurodegenerative disorders such as cerebral attacks (Eur J. Neurosci. 2005, 22(10), 2422-30; Glia.

2005, 52(4), 336-43; *J Neurosci.* 2006, 26(27), 7272-80; Brain 1999, 122(Pt8), 1449-68); *J Neurosci Res.* 2002, 67(4), 494-500).

The present invention relates also to a process for the preparation of compounds of formula I, starting from a compound of formula II, of trans relative configuration:

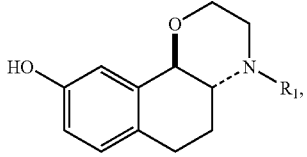

II wherein $R_1$ is as defined for formula I, which is reacted with triflic anhydride in the presence of pyridine to yield a compound of formula III:

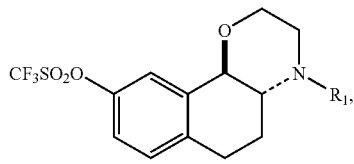

III wherein $R_1$ is as defined hereinbefore, which is reacted with zinc cyanide and tetrakis(triphenylphosphine)palladium(0) in dimethylformamide in the hot state to yield the compound of formula IV:

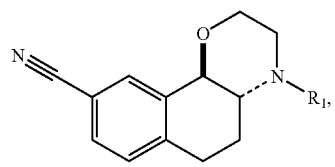

IV wherein $R_1$ is as defined hereinbefore, which is treated with a mixture of hydrochloric acid and acetic acid under reflux to yield a compound of formula V:

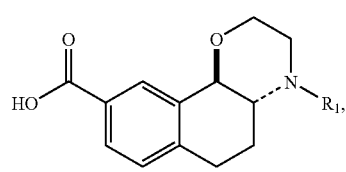

V wherein $R_1$ is as defined hereinbefore, which is then converted into a compound of formula I by conventional reactions of organic chemistry.

By way of example, the compounds of formula I wherein X represents NH and Y represents $CH_2$ can be obtained by reaction of a compound of formula V with diethylamine under conventional amidification conditions to yield a compound of formula VI:

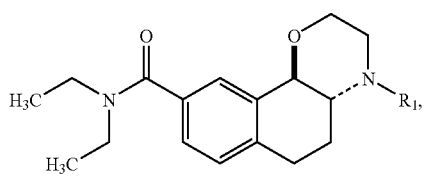

VI wherein $R_1$ is as defined hereinbefore, which is reacted with phenyl cyanate under orthometallation conditions to yield a compound of formula VII:

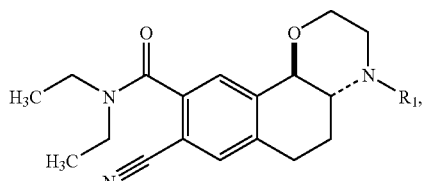

VII wherein $R_1$ is as defined hereinbefore, which is reduced with the aid of a conventional reducing agent such as, for example, Raney nickel to yield a compound of formula VIII:

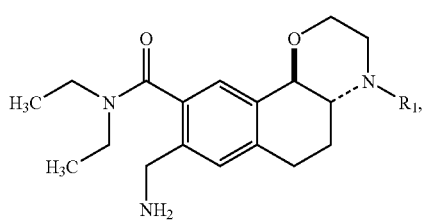

VIII wherein $R_1$ is as defined hereinbefore, which is cyclised in the presence of an organic lithium compound such as tert-butyllithium to yield the compounds of formula Ia, a particular case of the compounds of formula I:

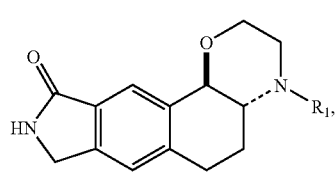

Ia wherein $R_1$ is as defined hereinbefore.

Compounds of formula I wherein X represents O and Y represents $CH_2$ can be obtained by reaction of a compound of formula VI with dimethylformamide, under orthometallation conditions, to yield a compound of formula IX:

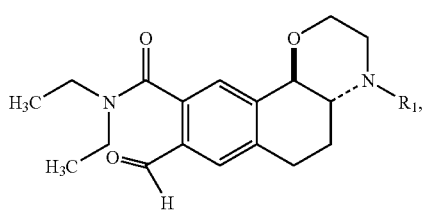

IX wherein R$_1$ is as defined hereinbefore, which is reduced with the aid of a selective reducing agent such as sodium borohydride to yield a compound of formula X:

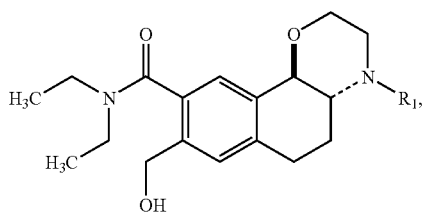

X wherein R$_1$ is as defined hereinbefore, which is cyclised in the presence of an organic or inorganic acid such as hydrochloric acid to yield the compounds of formula Ib, a particular case of the compounds of formula I:

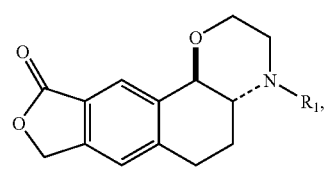

Ib wherein R$_1$ is as defined hereinbefore.

Compounds of formula I wherein X represents an NR'$_2$ group, wherein R'$_2$ represents a group selected from linear or branched C$_1$-C$_6$alkyl, C$_3$-C$_8$cycloalkyl, and cycloalkylalkyl wherein the alkyl moiety is C$_1$-C$_6$ and is linear or branched and the cycloalkyl moiety is C$_3$-C$_8$, and Y represents a CH$_2$ group, can be obtained by reaction of a compound of formula Ib with a primary amine of formula NH$_2$R'$_2$ to yield the compounds of formula Ic, a particular case of the compounds of formula I:

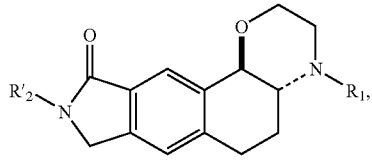

Ic wherein R$_1$ and R'$_2$ are as defined hereinbefore.

Compounds of formula I wherein X represents NH and Y represents —(CH$_2$)$_2$— can be obtained by reaction of a compound of formula X with a halogenating agent, such as thionyl chloride or thionyl bromide, or a compound of formula CG$_4$ in the presence of PPh$_3$, wherein G represents a chlorine, bromine or iodine atom, to yield a compound of formula XI:

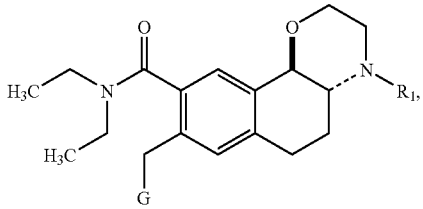

XI wherein R$_1$ is as defined hereinbefore and G represents a chlorine, bromine or iodine atom, which is reacted with a cyanating agent such as tetrabutylammonium cyanide, sodium cyanide or potassium cyanide to yield a compound of formula XII:

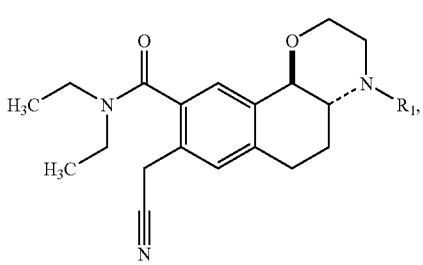

XII wherein R$_1$ is as defined hereinbefore, which is reduced with the aid of a conventional reducing agent such as Raney nickel to yield a compound of formula XIII:

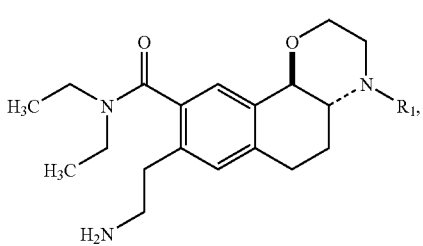

XIII wherein R$_1$ is as defined hereinbefore, which is cyclised with the aid of an organic lithium compound such as tert-butyllithium to yield a compound of formula Id, a particular case of the compounds of formula I:

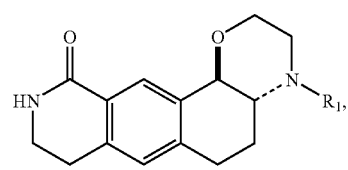

Id wherein R$_1$ is as defined hereinbefore.

Compounds of formula I wherein X represents O and Y represents —(CH$_2$)$_2$— can be obtained by reaction of a compound of formula VI with bromoethanol in the presence of n-butyllithium under orthometallation conditions to yield a compound of formula XIV:

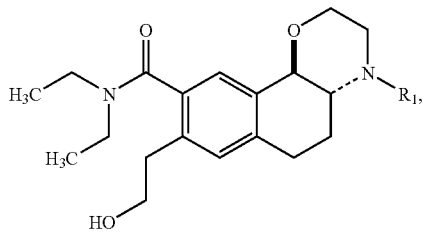

XIV wherein $R_1$ is as defined hereinbefore, which is cyclised with the aid of an organic or inorganic acid such as hydrochloric acid to yield the compounds of formula Ie, a particular case of the compounds of formula I:

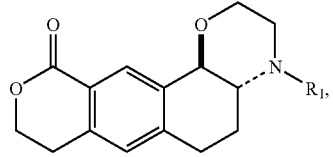

Ie wherein $R_1$ is as defined hereinbefore.

Compounds of formula I wherein X represents an $NR'_2$ group, wherein $R'_2$ represents a group selected from linear or branched $C_1$-$C_6$alkyl, $C_3$-$C_8$cycloalkyl, and cycloalkylalkyl wherein the alkyl moiety is $C_1$-$C_6$ and is linear or branched and the cycloalkyl moiety is $C_3$-$C_8$, and Y represents a —$(CH_2)_2$— group can be obtained by reaction of a compound of formula Ie with a primary amine of formula $NH_2R'_2$ to yield the compounds of formula If, a particular case of the compounds of formula I:

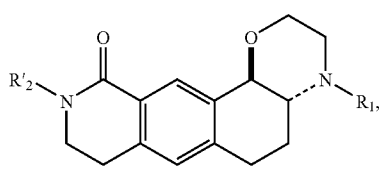

If wherein $R_1$ and $R'_2$ are as defined hereinbefore.

Compounds of formula I wherein X represents NH and Y represents CH=CH can be obtained by reaction of a compound of formula V with a chlorinating agent such as thionyl chloride to yield a compound of formula XV:

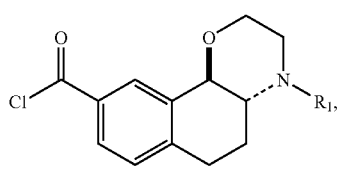

XV wherein $R_1$ is as defined hereinbefore, which is reacted with methoxylamine hydrochloride in the presence of a base such as potassium carbonate or sodium carbonate to yield a compound of formula XVI:

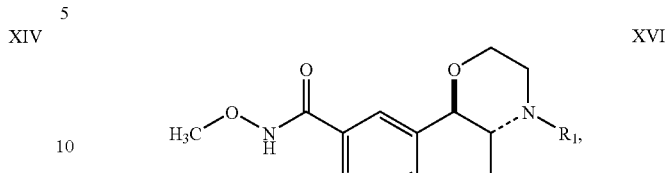

XVI wherein $R_1$ is as defined hereinbefore, which is reacted with methyl iodide under orthometallation conditions to yield a compound of formula XVII:

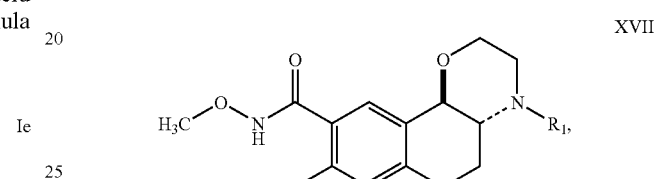

XVII wherein $R_1$ is as defined hereinbefore, which is reacted with dimethylformamide in the presence of an organic lithium compound such as sec-butyllithium to yield a compound of formula XVIII:

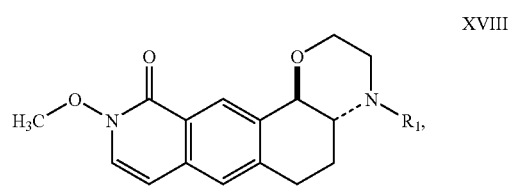

XVIII wherein $R_1$ is as defined hereinbefore, which is reacted with titanium(III) chloride to yield the compounds of formula Ig, a particular case of the compounds of formula I:

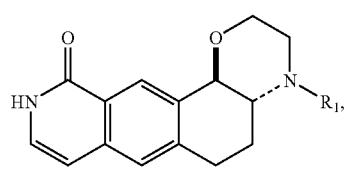

Ig wherein $R_1$ is as defined hereinbefore.

The starting compounds of formula II are prepared in accordance with procedures described in the literature, starting from known substances.

A (4aRS,11bRS) or (4aRS,10bRS) isomer is understood to be a racemic mixture of the enantiomers having the absolute configurations (4aR,11bR) and (4aS,11bS), or (4aR,10R) and (4aS,10bS), respectively.

The optically active forms of the compounds of formula I are obtained either by starting from optically active forms of the starting compounds of formula II or by resolving racemic forms of the compounds of formula I in accordance with methods known from the literature.

The compounds of the present invention are dopaminergic ligands. They are useful as medicaments in the treatment of disorders of the central nervous system that involve the dopaminergic system, such as Parkinson's disease, hyperprolactinaemia, sexual dysfunction, depression, anxiety, Alzheimer's disease and other neurodegenerative disorders such as cerebral attacks.

The present invention relates also to pharmaceutical compositions comprising as active ingredient a compound of formula I, or an addition salt thereof with a pharmaceutically acceptable acid, in combination with one or more inert, non-toxic, pharmaceutically acceptable excipients or carriers.

Among the pharmaceutical compositions according to the invention there may be mentioned more especially those that are suitable for oral, parenteral (intravenous, intramuscular or subcutaneous), per- or trans-cutaneous, nasal, rectal, perlingual, ocular or respiratory administration, and especially tablets or dragées, sublingual tablets, gelatin capsules, capsules, suppositories, creams, ointments, dermal gels, injectable or drinkable preparations, aerosols, eye drops and nose drops.

The useful dosage varies according to the age and weight of the patient, the administration route, the nature and severity of the disorder, and the administration of any associated treatments and ranges from 0.5 to 500 mg per day in one or more administrations.

The Examples that follow illustrate the present invention. The structures of the compounds described in the Examples were determined according to customary spectrophotometric techniques (infra-red, nuclear magnetic resonance, mass spectrometry).

EXAMPLE 1

(4aRS,11bRS)-4-Propyl-3,4,4a,5,6,8,9,11b-octahydroisoindolo[5,6-h][1,4]benzoxazin-10(2H)-one and its hydrochloride Step A (4aRS,10bRS)-N,N-Diethyl-4-propyl-3,4,4a, 5,6,10b-hexahydro-2H-naphtho[1,2-b][1,4]oxazine-9-carboxamide To 51 g (163 mmol) of trans-(4aRS,10bRS)-4-propyl-3,4, 4a,5,6,10b-hexahydro-2H-naphtho-[1,2-b][1,4]oxazine-9-carboxylic acid hydrochloride (prepared in accordance with the procedure described in patent specification EP 0 899 267), suspended in methylene chloride (815 ml), there are added, in succession, diethylamine (18.3 ml, 177 mmol, 1.09 eq.), O-benzotriazol-1-yl-N,N,N',N'-tetramethyluronium tetrafluoroborate (TBTU) (57 g, 177 mmol, 1.07 eq.) and then triethylamine (56 ml, 402 mmol, 2.4 eq.). The resulting solution is stirred at ambient temperature for 20 hours and then the reaction mixture is treated with 1N sodium hydroxide solution (425 ml). The organic phase is separated off, washed with saturated NaCl solution, dried over magnesium sulphate and then concentrated in vacuo. The residue obtained is purified by flash chromatography on silica gel using an eluant mixture of methylene chloride/ethanol (90/5). The expected product is collected in the form of an oil.

IR: 1629 cm$^{-1}$

N.M.R. $^1$H 300 MHz (CDCl$_3$): 7.60; 7.25; 7.10; 4.30; 4.10; 3.95; 3.7-3.15; 3.00-2.75; 2.50; 2.4-2.2; 1.7-1.4; 1.35-1.00; 0.95.

Step B (4aRS,10bRS)-N,N-Diethyl-8-cyano-4-propyl-3,4,4a,5,6,10b-hexahydro-2H-naphtho[1,2-b][1, 4]oxazine-9-carboxamide The amide obtained in the above Step (12 g, 36 mmol), dissolved in tetrahydrofuran (220 ml), is added to a solution, cooled to −78° C., of s-BuLi (1.3M) in hexane (40 ml) and of N,N,N',N'-tetramethylethylenediamine (TMEDA) (8.2 ml) in tetrahydrofuran (240 ml), while maintaining the internal temperature below −65° C. The resulting mixture is stirred for 1 hour 30 minutes at a temperature of −70° C. Phenyl cyanate (PhOCN) (12 g) is added, while maintaining the internal temperature below −65° C. The mixture is stirred for 5 minutes at −65° C., and the reaction mixture is then brought back to ambient temperature over 1 hour 30 minutes and then stirred at ambient temperature for 1 hour. The mixture is hydrolysed using a 10% solution of water in tetrahydrofuran, extracted with ethyl ether, dried and concentrated. The residue obtained is purified by flash chromatography on silica gel using an eluant mixture of methylene chloride/ethanol (95/5). The expected product is obtained in the form of an oil.

IR: 2228 cm$^{-1}$; 1632 cm$^{-1}$.

N.M.R. $^1$H 300 MHz (CDCl$_3$): 7.65; 7.40; 4.30; 4.05; 3.90; 3.60; 3.25; 3.05-2.75; 2.50-2.15; 1.8-1.4; 1.15; 0.95.

Step C: (4aRS,10bRS)-8-(Aminomethyl)-N,N-diethyl-4-propyl-3,4,4a,5,6,10b-hexahydro-2H-naphtho[1,2-b][1,4]oxazine-9-carboxamide The nitrile obtained in the above Step (0.61 g, 1.7 mmol), dissolved in methanol (60 ml), is treated with hydrogen under a pressure of 4 bar in the presence of Raney nickel (1 g), at 60° C. for 4 hours. After return to ambient temperature, the catalyst is filtered off; the filtrate is then concentrated. The residue obtained is purified by flash chromatography on silica gel using an eluant mixture of methylene chloride/ethanol/ammonia (90/10/1). The expected product is obtained in the form of an amorphous solid.

IR: 3388-3314 cm$^{-1}$, 1626 cm$^{-1}$.

N.M.R. $^1$H (CDCl$_3$): 7.35, s, 1H, 7.10, s, 1H, 4.30, d, 1H, 4.05, dd, 1H, 3.90, dt, 1H, 3.75, s, 2H, 3.55, q, 2H, 3.20, q, 1H; 2.85, m, 1H, 2.90, m, 2H, 2.80, m, 1H, 2.30, m, 1H, 2.30, m, 1H, 1.55, m, 1H, 1.50, m, 2H, 1.30, t, 3H, 1.05, t, 3H, 0.90, t, 3H.

Step D: (4aRS,11bRS)-4-Propyl-3,4,4a,5,6,8,9,11b-octahydroisoindolo[5,6-h][1,4]-benzoxazin-10(2H)-one and its hydrochloride A solution of tert-butyllithium (1.5M in pentane) (10 ml) is added to a solution of the amine obtained in the above Step (1.8 g) in tetrahydrofuran (200 ml). The resulting mixture is stirred for 15 minutes at −75° C. and for 20 minutes at −40° C. and is then hydrolysed using a 10% solution of water in tetrahydrofuran. After separation in the presence of methylene chloride, drying and concentrating under reduced pressure, the expected product is isolated in the form of a white solid, the hydrochloride of which is crystallised from methanol.

IR: 1691 cm$^{-1}$; 3183 cm$^{-1}$.

N.M.R. $^1$H 300 MHz (CDCl$_3$): 8.09, s, 1H, 7.16, s, 1H, 6.68, unresolved peak, 1H, 4.38, m, 1H, 4.35, d, 1H, 4.09, m, 1H, 3.95, td, 1H, 3.00, m, 2H, 2.89, d, 1H, 2.82, m, 1H, 2.46, td, 1H, 2.29, m, 3H, 1.64, m, 1H, 1.53, m, 2H; 0.92, t, 3H.

EXAMPLE 2

(4aR,11bR)-4-Propyl-3,4,4a,5,6,8,9,11b-octahydroisoindolo[5,6-h][1,4]-benzoxazin-10(2H)-one and its hydrochloride 700 mg of the product obtained in Step D of Example 1 are placed on a Chiralcel® OD column and separated by HPLC, using a 200:1 mixture of isopropanol and trifluoroacetic acid as mobile phase. The expected product is the first to be eluted. After treatment with sodium hydroxide and then with 2M ethereal hydrogen chloride solution, the hydrochloride of the expected product is obtained.

Melting point: 287-291° C.
Optical rotation: solvent=methanol
conc.=1%
temp.=20° C.
λ.=589 nm
D=+52.4

EXAMPLE 3

(4aS,11bS)-4-Propyl-3,4,4a,5,6,8,9,11b-octahydroisoindolo[5,6-h][1,4]-benzoxazin-10(2H)-one and its hydrochloride The second product eluted in Example 2 corresponds to the expected product. After treatment with sodium hydroxide and then with 2M ethereal hydrogen chloride solution, the hydrochloride of the expected product is obtained.

Melting point: 302-308° C.
Optical rotation: solvent=methanol
conc.=1%
temp.=20° C.
λ.=589 nm
D=−53.9

EXAMPLE 4

(4aR,11bR)-4-Propyl-2,3,4,4a,5,6,8,11b-octahydro-10H-furo[3',4':6,7]-naphtho[1,2-b][1,4]oxazin-10-one and its hydrochloride Step A: (4aR,10bR)-N,N-Diethyl-4-propyl-3,4,4a,5,6,10b-hexahydro-2H-naphtho[1,2-b][1,4]-oxazine-9-carboxamide (4aR,10bR)-N,N-Diethyl-4-propyl-3,4,4a,5,6,10b-hexahydro-2H-naphtho[1,2-b][1,4]oxazine-9-carboxylic acid hydrochloride ($\alpha_D$=+90.6, at 20° C., 1% concentration in methanol) is treated as in Step A of Example 1 to yield the expected product.

Step B (4aR,10bR)-N,N-Diethyl-8-formyl-4-propyl-3,4,4a,5,6,10b-hexahydro-2H-naphtho-[1,2-b][1,4]oxazine-9-carboxamide The amide obtained in the above Step (2 g, 6.05 mmol), dissolved in tetrahydrofuran (10 ml), is added to a solution, cooled to −78° C., of s-BuLi (1.3M, 7.86 ml) and of N,N,N',N'-tetramethylethylenediamine (TMEDA) (1.2 ml, 7.9 mmol) in tetrahydrofuran (25 ml), while maintaining the temperature below −65° C. throughout. The resulting mixture is stirred for 1 hour 30 minutes, and then N,N-dimethylformamide (1 ml) is added while maintaining the internal temperature below −65° C. The mixture is stirred for 5 minutes at −65° C.; the reaction mixture is then brought back to ambient temperature over 1 hour 30 minutes and is stirred for 1 hour at that temperature.

After hydrolysis using a 10% solution of water in tetrahydrofuran, extraction with ethyl ether, drying and concentration, the residue obtained is purified by flash chromatography on silica gel using an eluant mixture (methylene chloride/ethanol:95/5). The expected product is collected in the form of an oil.

IR: 2940-1696 cm$^{-1}$; 1628 cm$^{-1}$.
N.M.R. $^1$H 300 MHz (CDCl$_3$): 9.90, s, 1H, 7.70, s, 1H, 6.30, s, 1H, 4.25, d, 1H, 4.00, m, 1H, 3.80, m, 1H, 3.45, q, 2H, 3.00, q, 2H, 3.00-2.70, m, 4H, 2.35-2.05, m, 4H, 1.45, m, 3H, 1.20, t, 3H, 0.90, t, 3H, 0.85, t, 3H.

Step C: (4aR,11bR)-4-Propyl-2,3,4,4a,5,6,8,11b-octahydro-10H-furo[3',4':6,7]naphtho-[1,2-b][1,4]oxazin-10-one and its hydrochloride The aldehyde obtained in the above Step (3.5 g) is dissolved in methanol (35 ml). The solution, cooled to 0° C., is treated with sodium borohydride (0.45 g). The reaction mixture is stirred for 20 hours, accompanied by return to ambient temperature. The reaction mixture is cooled to 0° C.; a 6N hydrochloric acid solution (7 ml) is then added. The resulting mixture is heated at reflux for 20 hours. After return to ambient temperature, the hydrochloride of the expected product is isolated and recrystallised from methanol.

Melting point: 268-271° C.
IR: 2780 cm$^{-1}$, 2140 cm$^{-1}$, 1746 cm$^{-1}$.
N.M.R. $^1$H 300 MHz (DMSO-d6): 11.90, m, 1H, 7.80, s, 1H, 7.50, s, 1H, 5.40, s, 2H, 5.10, d, 1H, 4.25, m, 2H, 3.60, m, 1H, 3.45-3.15, m, 3H, 3.15-2.95, m, 3H, 2.55, m, 1H, 2.10, m, 1H, 1.75 (sext), 2H, 0.95 (t), 3H.

EXAMPLE 5

(4aR,12bR)-4-Propyl-3,4,4a,5,6,8,9,12b-octahydro-2H,11H-pyrano-[4',3':6,7]naphtho[1,2-b][1,4]oxazin-11-one and its hydrochloride Step A: (4aR,10bR)-8-(2-Hydroxyethyl)-N,N-diethyl-4-propyl-3,4,4a,5,6,10b-hexahydro-2H-naphtho[1,2-b][1,4]oxazine-9-carboxamide The amide obtained in Step A of Example 4 (5 g, 15 mM), dissolved in tetrahydrofuran (60 ml), is added to a solution, cooled to −78° C., of s-BuLi (1.3M) in hexane (14.7 ml) and of N,N,N',N'-tetramethylethylenediamine (TMEDA) (3 ml) in tetrahydrofuran (65 ml), while maintaining the internal temperature below −65° C. The resulting mixture is stirred for 30 minutes at a temperature of −70° C. A solution of lithiated bromoethanol [prepared from bromoethanol and n-BuLi (2.5M in hexane) in tetrahydrofuran] is transferred by cannula, while maintaining the internal temperature below −65° C. The mixture is stirred for 5 minutes at −65° C.; the reaction mixture is brought back to ambient temperature over 1 hour 30 minutes and stirring is continued for 1 hour more. Hydrolysis using a 10% solution of water in tetrahydrofuran, extraction with methylene chloride, drying and concentration are carried out. The residue obtained is purified by flash chromatography on silica gel using an eluant mixture of methylene chloride/ethanol (90/10). The expected product is isolated in the form of an oil.

IR: 3600-3090 cm$^{-1}$; 1621 cm$^{-1}$.

N.M.R. $^1$H 300 MHz (DMSO-d6): 7.10, s, 1H, 7.00, s, 1H, 4.60, t, 1H, 4.15, d, 1H, 3.95, d, 1H, 3.75, t, 1H, 3.50, m, 2H, 3.40, m, 2H, 3.05, m, 2H, 2.80, m, 2H, 2.60, m, 2H, 2.30-2.00, m, 5H, 1.55-1.35, m, 4H, 1.15, t, 3H, 0.95, t, 3H, 0.85, t, 3H.

Step B: (4aR,12bR)-4-Propyl-3,4,4a,5,6,8,9,12b-octahydro-2H,11H-pyrano[4',3':6,7]-naphtho[1,2-b][1,4]oxazin-11-one and its hydrochloride 6N hydrochloric acid solution (2.1 ml) is added at ambient temperature to a solution of the product obtained in the above Step (1.08 g, 2.88 mmol) in methanol (9 ml). The resulting mixture is heated at reflux for 20 hours. After return to ambient temperature, filtration of the precipitate formed allows the hydrochloride of the expected product to be obtained.

Melting point: 275-279° C.

IR: 2401 cm$^{-1}$, 1712 cm$^{-1}$, 1620 cm$^{-1}$.

N.M.R. $^1$H 300 MHz (DMSO-d6): 11.50, m, 1H, 8.00, s, 1H, 7.21, s, 1H, 4.95, dd, 1H, 4.50, t, 2H, 4.25, d, 2H, 3.60, m, 1H, 3.28, m, 3H, 3.05, m, 5H, 2.50, m, 1H, 2.00, m, 1H, 1.75, m, 2H, 1.00, t, 3H.

EXAMPLE 6

(4aR,12bR)-4-Propyl-2,3,4,4a,5,6,8,9,10,12b-decahydro-11H-isoquino-[6,7-h][1,4]benzoxazin-11-one and its hydrochloride Step A: (4aR,10bR)-8-Hydroxymethyl-N,N-diethyl-4-propyl-3,4,4a,5,6,10b-hexahydro-2H-naphtho[1,2-b][1,4]oxazine-9-carboxamide The aldehyde obtained in Step B of Example 4 (0.85 g, 2.4 mmol) is dissolved in methanol (10 ml). The solution, cooled to 0° C., is treated with sodium borohydride (0.16 g, 4.23 mmol). The reaction mixture is stirred for 20 hours accompanied by return to ambient temperature. The methanol is evaporated off in vacuo. The residue is taken up in water and methylene chloride. After separation, drying and concentration, the residue obtained is purified by flash chromatography on silica gel using an eluant mixture of methylene chloride/ethanol (95/5). The expected product is obtained in the form of an oil.

IR: 3600-3070 cm$^{-1}$; 1627 cm$^{-1}$.

N.M.R. $^1$H 300 MHz (DMSO-d6): 7.20, s, 1H, 7.10, s, 1H, 5.10, t, 1H; 4.35, d, 1H, 4.20, d, 1H, 4.00, m, 1H; 3.80, m, 1H; 3.40, q, 2H, 3.10, q, 2H, 2.80, m, 4H, 2.40-2.00, m, 4H, 1.45, m, 3H, 1.10, t, 3H; 0.95, t, 3H; 0.85, t, 3H.

Step B: (4aR,10bR)-8-Chloromethyl-N,N-diethyl-4-propyl-3,4,4a,5,6,10b-hexahydro-2H-naphtho[1,2-b][1,4]oxazine-9-carboxamide The alcohol obtained in the above Step, dissolved in toluene, is treated with thionyl chloride (0.4 ml). The mixture is stirred at ambient temperature for 20 hours. The toluene is evaporated off in vacuo. The residue is taken up in water and methylene chloride. After separation, washing with aqueous sodium bicarbonate solution and drying, the expected compound is obtained in the form of an oil.

IR: 1627 cm$^{-1}$.

N.M.R. $^1$H 300 MHz (DMSO-d6): 7.25, s, 1H, 7.20, s, 1H, 4.65, d, 1H, 4.20, d, 1H, 4.00, dd, 1H, 3.80, td, 1H, 3.45, q, 2H, 3.10, q, 2H, 2.90-2.70, m, 4H, 2.40-2.05, m, 4H, 1.6-1.35, m, 3H, 1.25, t, 3H, 1.00, t, 3H; 0.90, t, 3H.

Step C: (4aR,10bR)-8-Cyanomethyl-N,N-diethyl-4-propyl-3,4,4a,5,6,10b-hexahydro-2H-naphtho[1,2-b][1,4]oxazine-9-carboxamide The compound obtained in the above Step (0.64 g, 1.68 mmol), dissolved in tetrahydrofuran (15 ml), is treated with tetrabutylammonium cyanide (0.8 g, 2.98 mmol) for 20 hours. The mixture is concentrated in vacuo. The residue is taken up in water and methylene chloride. After separation, drying and then concentration, the expected nitrile is obtained in the form of an oil.

IR: 1628 cm$^{-1}$.

N.M.R. $^1$H 300 MHz (DMSO-d6): 7.20, 2s, 2H, 4.20, d, 11H, 4.00, dd, 11H, 3.80, m+s, 3H, 3.45, q, 2H, 3.10, q, 2H, 2.90-2.70, m, 4H, 2.35-2.05, m, 4H, 1.55-1.35, m, 3H, 1.15, t, 3H, 1.00, t, 3H; 0.85, t, 3H.

Step D: (4aR,10bR)-8-(2-Aminoethyl)-N,N-diethyl-4-propyl-3,4,4a,5,6,10b-hexahydro-2H-naphtho[1,2-b][1,4]oxazine-9-carboxamide The compound obtained in the above Step (2.7 g, 7.3 mmol), dissolved in methanol (250 ml), is treated with hydrogen under a pressure of 4 bar in the presence of Raney nickel (1 g), at 60° C., for 4 hours. After return to ambient temperature, the catalyst is filtered off; the filtrate is then concentrated. The residue obtained is purified by flash chromatography on silica gel using an eluant mixture of methylene chloride/ethanol/ammonia (90/10/1). The expected product is isolated in the form of an amorphous solid.

IR: 3360-3310 cm$^{-1}$, 1626 cm$^{-1}$.

N.M.R. $^1$H 300 MHz (DMSO-d6): 7.10, s, 1H, 7.00, s, 1H, 4.20, d, 1H, 4.00, m, 1H, 3.80, m, 1H, 3.45, q, 2H, 3.10, q, 2H, 2.9-2.7, m, 4H, 2.50, m, 2H, 2.4-2.05, m, 4H, 1.6-1.3, m, 3H, 1.20, t, 3H, 1.00, t, 3H; 0.90, t, 3H.

Step E: (4aR,12bR)-4-Propyl-2,3,4,4a,5,6,8,9,10,12b-decahydro-11H-isoquino[6,7-h][1,4]-benzoxazin-11-one and its hydrochloride A 1.5M solution of tert-butyllithium in pentane (1.9 ml, 3.21 mmol) is added to a solution of the amine obtained in the above Step (0.40 g) in tetrahydrofuran (45 ml). The resulting mixture is stirred for 10 minutes at −78° C., and then for 20 minutes at −40° C. The mixture is hydrolysed using a 10% solution of water in tetrahydrofuran. After separation in the presence of methylene chloride, drying and concentration under reduced pressure, the residue obtained is purified by flash chromatography on silica gel using an eluant mixture of methylene chloride/ethanol (90/10). The expected product is isolated in the form of an amorphous solid, the hydrochloride of which is crystallised from ethyl acetate.

Melting point: 263-265° C.

IR: 1666 cm$^{-1}$.

N.M.R. $^1$H (DMSO-d6): 7.90, s, 1H, 7.10, s, 1H, 5.00, d, 1H, 4.25, m, 2H, 3.60, m, 1H, 3.4-3.15, m, 5H, 3.00, m, 3H, 2.85, m, 2H, 2.50, m, 2H, 2.00, m, 1H, 1.75, m, 2H, 1.00, t, 3H.

EXAMPLE 7

(4aR,11bR)-9-Methyl-4-propyl-3,4,4a,5,6,8,9,11b-octahydroisoindolo-[5,6-h][1,4]benzoxazin-10(2H)-one and its hydrochloride The product of Example 4 (1 g, 3.08 mmol), dissolved in a 40% aqueous methylamine solution (10 ml), is heated in an autoclave for 16 hours at 120° C. After return to ambient temperature, the mixture is extracted with methylene chloride; the organic phase is dried over MgSO$_4$. Concentration yields a residue which is purified by flash chromatography on silica gel using an eluant mixture of methylene chloride/ethanol (95/5). The expected product is obtained in the form of a white solid, the hydrochloride of which is crystallised from acetonitrile.

Melting Point: 240-245° C.

IR: 1692 cm$^{-1}$.

N.M.R. $^1$H 300 MHz (DMSO-d6): 8.00, s, 1H, 7.10, s, 1H, 4.35, d, 1H; 4,30, s, 2H, 4.10, m, 1H, 3.95, m, 1H, 3.20, s, 3H, 3.00, m, 2H, 2.90, m, 1H, 2.85, m, 1H, 2.50, m, 1H; 2,30, m, 3H, 1.7-1.4, m, 3H; 0.90, t, 3H.

EXAMPLE 8

(4aR,12bR)-4-Propyl-2,3,4,4a,5,6,10,12b-octahydro-11H-isoquino-[6,7-h][1,4]benzoxazin-11-one and its hydrochloride Step A: (4aR,10bR)-9-(4-Propyl-3,4,4a,5,6,10b-hexahydro-2H-naphtho[1,2-b][1,4]oxazine)-carboxylic acid chloride 3.6 ml (41.7 mmol) of thionyl chloride are added dropwise to (4aR,10R)-4-propyl-3,4,4a,5,6,10b-hexahydro-2H-naphtho[1,2-b][1,4]oxazine-9-carboxylic acid (10 g, 32 mmol), suspended in anhydrous toluene (100 ml) and dimethylformamide (0.15 ml). The resulting mixture is heated at reflux for 1 hour. After return to ambient temperature, the mixture is filtered; the solid residue is washed with toluene. The solid is dried to constant weight in an oven in vacuo in the presence of P$_2$O$_5$ to yield the expected product.

IR: 2457 cm$^{-1}$; 1753 cm$^{-1}$; 814-775 cm$^{-1}$.

N.M.R. $^1$H 300 MHz (DMSO-d6): 8.05 (s) 1H, 7.80 (dd) 1H, 7.30 (d) 1H, 5.05 (d) 1H, 4.30 (m) 2H, 3.60 (d) 1H, 3.50 (NH) 1H, 3.30 (m) 3H, 3.00 (m) 3H, 2.50 (m) 1H, 2.10 (m) 1H, 1.75 (m) 2H; 0.95 (t) 3H.

Step B: (4aR,10bR)-9-(4-Propyl-3,4,4a,5,6,10b-hexahydro-2H-naphtho[1,2-b][1,4]oxazine)-carboxylic acid methoxy methyl amide 2.62 g (31.3 mmol) of methoxylamine hydrochloride are added to a mixture of potassium carbonate (13 g, 94 mmol) in water (31 ml) and ethyl acetate (62 ml). To the mixture, cooled to 0° C., there is added, in portions, the acid chloride of Step A (10.35 g, 31.3 mmol), while maintaining the temperature below 5° C. The mixture is stirred for 2 hours at 0° C. After adding ethyl acetate and water and return to ambient temperature, the mixture is separated; the organic phase is washed with water, dried over magnesium sulphate and then concentrated in vacuo to yield the expected product in the form of a solid.

Melting point: 147-152° C.

IR: 3194 cm$^{-1}$, 2870 cm$^{-1}$, 2803-2767 cm$^{-1}$, 1650 cm$^{-1}$, 1272-1126 cm$^{-1}$, 834-760 cm$^{-1}$.

N.M.R. $^1$H 300 MHz (DMSO-d6): 11.60 (s) 1H, 7.82 (s) 1H, 7.55 (dd) 1H, 7.18 (d) 1H, 4.20 (d) 1H, 4.00 (dd) 1H, 3.80 (td) 1H, 2.7 to 3.00 (m) 3H, 2.30 (m) 2H, 2.05 to 2.2 (m) 2H, 1.45 (m) 3H; 0.88 (t) 3H.

Step C: (4aR,12bR)-10-Methoxy-4-propyl-2,3,4,4a,5,6,10,12b-octahydro-11H-isoquino[6,7-h][1,4]benzoxazin-11-one A solution of the amide obtained in Step B (4 g, 13.14 mmol) in tetrahydrofuran (40 ml) is added to a solution, cooled to –78° C., of s-BuLi (24 ml, 31.53 mM) and of N,N,N',N'-tetramethylethylenediamine (TMEDA) (4.8 ml, 31.53 mmol) in tetrahydrofuran (90 ml), while maintaining the temperature below –70° C. The reaction mixture is brought back to a temperature of –20° C. and is then stirred for 45 minutes at an average temperature of –10° C. The mixture is again cooled to –78° C. and methyl iodide (0.9 ml, 14.45 ml) is added. The temperature is brought back to 0° C. and then to ambient temperature. Hydrolysis is carried out using saturated ammonium chloride solution. After adding ethyl ether, the mixture is separated; the organic phase is washed with water, dried over magnesium sulphate and then concentrated in vacuo. A solution of s-BuLi (21.4 ml, 27.8 mmol) is added to a solution of the resulting residue (4.04 g) in tetrahydrofuran (83 ml). Cooling to –78° C. and stirring for 2 hours at that temperature are carried out. While maintaining the temperature below –70° C., dimethylformamide (1.13 ml, 14.6 mmol) is added to the mixture, which is stirred for 10 minutes at that temperature before being brought back to ambient temperature. Hydrolysis is carried out using saturated ammonium chloride solution. After adding ethyl ether, the mixture is separated; the organic phase is washed with water, dried over magnesium sulphate and then concentrated in vacuo. The residue is taken up in tetrahydrofuran (330 ml), concentrated hydrochloric acid is added (13.5 ml) and the mixture is stirred for 1 hour at ambient temperature. After treating with concentrated sodium hydroxide solution, extracting with ethyl acetate and washing with water and with sodium chloride solution, the organic phase is dried over magnesium sulphate and then concentrated in vacuo. The residue obtained is purified by flash chromatography on silica gel using an eluant mixture of methylene chloride/ethanol (95/5). The expected product is isolated in the form of a beige solid.

Melting point: 142-145° C.

N.M.R. $^1$H 400 MHz (CDCl$_3$): 8.65, 7.25, 7.22, 6.35, 4.47, 4.12-4.03, 4.05, 3.00 ppm Step D: (4aR,12bR)-4-Propyl-2,3,4,4a,5,6,10,12b-octahydro-11H-isoquino[6,7-h][1,4]-benzoxazin-11-one and its hydrochloride A 15% solution of TiCl$_3$ in water (7.6 ml) is added to a solution of the compound of Step C (1.1 g, 3.35 mmol) in ethanol (3.3 ml). The reaction mixture is heated at 45° C. for 24 hours. Heating is continued for 6 days with daily additions of 15% TiCl$_3$ solution (3.5 ml). After return to ambient temperature, the mixture is treated with water (30 ml) and ice (30 g) and is then rendered alkaline at pH 13-14 using 35% sodium hydroxide solution. The black suspension is treated with a current of compressed air until it has been decolourised completely. After extraction with methylene chloride, drying and concentration, the residue obtained is purified by flash chromatography on silica gel using an eluant mixture of methylene chloride/ethanol (95/5). The expected product is isolated in the form of a white solid, the hydrochloride of which is crystallised from acetonitrile.

Melting point: 200-203° C.

IR: 3457 cm$^{-1}$, 3162 cm$^{-1}$, 1632 cm$^{-1}$.

N.M.R. 1H 400 MHz (DMSO-d6): 11.10 (m) 2H, 8.25 (s) 1H, 7.40 (s) 1H, 7.10 (t) 1H, 6.40 (d) 1H; 4.95 (d) 1H, 4.25 (m) 2H, 3.60 (d) 1H, 3.3-3.0 (2m) 2H; 3.0.5-2.00 (2m) 4H, 1.70 (m) 2H; 0.95 (t) 3H.

PHARMACOLOGICAL STUDY

EXAMPLE 9

Human $D_2$ and $D_3$ Receptor Binding Study

Cell Culture

CHO (Chinese Hamster Ovary) cells are stably transfected with the gene encoding the human dopamine $D_2$ or $D_3$ receptor, in accordance with methods known from the literature. The native cells are deficient in the enzyme DHFR (DiHydroFolate Reductase). The cells are cultured in an incubator at 37° C. in a humid atmosphere of 5% $CO_2$, 95% air. The transfections are carried out using Lipofectin (Gibco). The CHO cells co-transfected with the human $D_2$ receptor and the phleomycin resistance gene are selected for their resistance to the presence of that antibiotic in the culture medium. The cells transfected with the human $D_3$ receptor are selected, in a medium lacking hypoxanthine/thymidine, in the presence of methotrexate. The compositions of the culture media used are: for CHO-$D_2$, DMEM (Dulbecco's Modified Eagle Medium) supplemented with 10% foetal calf serum and hypoxanthine/thymidine; and for CHO-$D_3$, DMEM supplemented with 10% dialysed foetal calf serum. The cells are harvested at confluence and the membranes are then prepared.

Membrane Preparation:

After a few minutes in the presence of 0.2% trypsin, the cells are collected and centrifuged at 2,000 g for 5 minutes. The cell mass, which is re-suspended in 10 mM Tris-HCl buffer pH 7.5 containing 5 mM $MgSO_4$, is then homogenised using a Polytron®. The homogenate is then centrifuged at 50,000 g for 15 minutes, and the sediment is re-suspended by gentle sonication in an incubation buffer having the composition: 50 mM Tris-HCl pH 7.5 containing 120 mM NaCl, 5 mM KCl, 2 mM $CaCl_2$, 5 mM $MgCl_2$. The membranes are then divided into aliquots and stored at −80° C. until the day of the experiment.

Binding Experiments

Incubation is carried out in polypropylene tubes at a final volume of 400 μl containing:
100 μl of [$^{125}$I]-iodosulpride (Amersham) at 0.1 nM and 0.2 nM for the $D_2$ and $D_3$ receptors, respectively
100 μl of buffer (total tubes)
or 100 μl of 10 μM raclopride (non-specific binding)
or 100 μl of compound
200 μl of membrane preparation containing the $D_2$ or $D_3$ receptors in buffer to which 0.2% BSA (bovine serum albumin) has been added.

The concentration ranges of each compound include at least seven points determined in triplicate. Each experiment is repeated at least twice.

The incubation, which lasts for thirty minutes at 30° C., is terminated by rapid filtering through a Brandle apparatus, followed by three consecutive rinsings with Tris-HCl buffer pH 7.4 containing 120 mM NaCl. The filters are collected and then subjected to counting using a gamma counter.

Analysis of Results

The $IC_{50}$, representing the concentration producing 50% inhibition of the binding of the radioligand, is calculated by non-linear regression (Prism Graph method).

The $K_i$ value is derived from the formula $K_i = IC_{50}/(1+L/Kd)$ where L is the concentration of [$^{125}$I]-iodosulpride used in the experiment and Kd is its dissociation constant. The results are expressed in the form of $pK_i$ ($pK_i = -\log K_i$).

For the human $D_2$ and $D_3$ receptors, the Kd values are 0.5 nM and 1.3 mM, respectively.

Results

| Compound | $pK_i$ | |
|---|---|---|
| | $hD_3$ | $hD_2$ |
| Example 1 | 8.1 | 5.9 |
| Example 2 | 8.4 | 6.1 |
| Example 4 | 8.1 | 5.7 |
| Example 5 | 6.9 | 5.8 |
| Example 6 | 7.4 | 6.1 |
| Example 8 | 7.7 | 5.9 |

EXAMPLE 10

Presynaptic Dopaminergic Autoreceptor Activation

Test Recording the Unitary Extracellular Electrical Activity in the Ventral Tegmentum Area of the Rat Principle Administration of a dopaminergic agonist decreases neuron discharge frequency in dose-dependent manner. This effect is reversed by haloperidol, a dopaminergic antagonist.

Method

The rats are anaesthetised using chloral hydrate (400 mg/kg, i.p.) and placed in a stereotactic apparatus (Uniméca-nique, France) after catheterisation of the femoral vein. The level of anaesthesia is maintained by i.p. administration of chloral hydrate every hour; rectal temperature is held at 37±1° C. by means of a thermostatically controlled heated blanket. A tungsten microelectrode (10 MΩ, 1 μm) is advanced, using an electronic microdrive (Unimécanique, France), into the ventral tegmentum area (AP: −5.5/bregma; L: 0.7; H: 7.0-8.5/dura; Paxinos and Watson atlas, 1986). The potentials of dopaminergic cells are recognised by their morphology (triphasic potentials +/−/+, of a duration greater than 3 msec), their discharge rhythm, whether regular or in bursts of decreasing amplitude, and their discharge frequency, which is from 2 to 8 Hz. A single cell per animal is used for recording.

After a period $\geq 5$ minutes (basal activity) and an initial injection of carrier (distilled water to which a few drops of dilute lactic acid have been added; pH adjusted to 5 using 1N NaOH), the products of the invention are administered intravenously in cumulatively increasing doses at intervals of 2-3 minutes.

Analysis of Results

Data acquisition is performed by the Spike2 software package (Cambridge Electronic Design, England). The discharge frequency is measured over one minute at the maximum change between each injection and is expressed as the percentage change with respect to the basal activity (averaged over the 5 minutes preceding the first treatment), which is defined as 100%. The effect of the products is statistically evaluated by analysis of variance over repeated measurements, followed by a Dunnett's test for comparison of the effects of different doses with the effect of the carrier (distilled water).

Results

By way of example, the following Table shows the effects of the product of Example 2.

| Example 2 - dose µg/kg i.v. | Neuron discharge frequency |
|---|---|
| carrier (0) | 102.6 ± 0.9 |
| 0.125 | 91.8 ± 5.2 |
| 0.25 | 79.9 ± 5.9* |
| 0.5 | 66.3 ± 5.9* |
| 1.0 | 42.0 ± 7.3* |
| 2.0 | 10.8 ± 8.7* |
| 4.0 | 2.3 ± 2.3* |
| 8.0 | 0.0 ± 0.0* |

Individual values (n = 5) = mean ± standard error of the mean.
*= p < 0.05 versus carrier

EXAMPLE 11

Antidepressive Properties: Forced Swimming Test in the Rat

Principle

The forced swimming test (Porsolt R. et al, *Eur. J. Pharmacol.*, 1978, 47, 379-91) is a behavioural test which comprises inducing a state of "despair" in the rat, by placing the naive animal in an enclosure full of water, from which it cannot escape, for a period of fifteen minutes. For the first five to ten minutes, the rat struggles vigorously but finally adopts an immobile posture during the last part of the test. Placed in the same enclosure on the following day, the animal remains immobile for most of the test (5 minutes' duration). Antidepressants reduce the duration of immobility of the rat during the test.

Experiment Procedure

The experiment is carried out over two days, with a 24-hour interval, on rats having an average weight of 170 g, housed the day before in individual cages, with free access to food and drink.

On the first day, each rat is placed for fifteen minutes in a glass cylinder (20 cm diameter×40 cm high) filled to a height of 15 cm with water maintained at 25° C. On the second day, the animal is again placed in a cylinder for a period of five minutes; the total period of immobility (in seconds) of the rat is measured. The product or the solvent is administered to the animal thirty minutes before the beginning of the test. The effect of the products is statistically evaluated by analysis of variance over repeated measurements, followed by a Dunnett's test for comparison of the effects of different doses with the effect of the carrier (distilled water).

Results

By way of example, and to illustrate the activity of the products of the invention, the effects of the product of Example 2 are listed in the following Table:

| Product | Dose mg/kg s.c. | Immobility (sec) mean ± s.e.m. |
|---|---|---|
| Carrier (distilled water) | 0 | 174.3 ± 9.1 |
| Example 2 | 0.02 | 159.4 ± 7.9 |
| | 0.04 | 122.7 ± 21.2* |
| | 0.08 | 22.03 ± 5.8* |

*p < 0.05 versus carrier - s.e.m. = standard error relative to the mean

The product of Example 2 reduces the period of immobility of the animal in dose-dependent manner and accordingly exhibits an excellent antidepressant effect.

EXAMPLE 12

Rotations Induced by Dopaminergic Agonists in Rats Having a Unilateral Lesion of the *Substantia nigra*

Principle

Unilateral injection of the neurotoxin 6-hydroxy-dopamine (6-OH-DA) into the *Substantia nigra* produces degeneration of the ascending nigrostriatal pathways, with hypersensitivity of the post-synaptic dopaminergic receptors on the same side as the lesion. In a rat subjected to such a lesion, systemic administration of direct agonist products (apomorphine) induces contralateral rotations (rotation on the opposite side to the lesion). This test makes it possible to demonstrate the agonist dopaminergic properties of products targeted at therapy in Parkinson's disease.

Methods

Lesion: the lesion is produced in male Wistar rats weighing from 280 to 330 g, anaesthetised using pentobarbital (40-50 mg/kg i.p.) and having received a dose of 25 mg/kg i.p. of desipramine. The animal is placed in a KOPF stereotactic apparatus, with the cranium oriented in accordance with the Pellegrino and Cushman Atlas (1979). A volume of 4 µl of a solution of 6-OH-DA (2 µg/µl) is slowly injected, using a microperfuser, into the left *Substantia nigra*, (A=2.4 mm; L=2.0 mm; V=3.1 mm, relative to the interaural zero) (U. Ungerstedt, *Acta Physiol. Scandi. Suppl.*, 1971, 367, 69-93)

Apparatus: recording of the number and direction of rotations is performed automatically by computer using the ROTACOUNT system (Columbus Colo., USA). The animal is placed in a flat-bottomed cylinder 30 cm in diameter and 50 cm in height. A fine, semi-rigid cable is passed around the animal below the front paws and is connected to an optical counting cell which is located above the cylinder and connected to the computer.

Selection of lesioned animals: one month after inducing the lesion with 6-OH-DA, the correctly lesioned animals are selected according to a criterion of at least 150 contralateral rotations performed in the course of 1 hour after administration of the dopaminergic agonist apomorphine (0.04 mg/kg, s.c.).

Experiment procedure: the animals are tested once per week, the products of the invention being administered in alternation with the dopaminergic agonist. Recording of the contralateral rotations starts on injection of the dopaminergic agonist (T0) and lasts for one hour. The effect of the products is statistically evaluated by analysis of variance over repeated measurements, followed by a Dunnett's test for comparison of the effects of different doses with the effect of the carrier (distilled water).

Results

By way of example, the following Table shows the effect of the product of Example 2 administered by the s.c. route.

| Product | Dose mg/kg s.c. | Contralateral rotations mean ± s.e.m. (n) |
|---|---|---|
| Carrier (distilled water) | 0 | 53.8 ± 12.8 (8) |
| Apomorphine | 0.02 | 497.2 ± 91.4 * (11) |
| Example 2 | 0.00063 | 157.4 ± 32.1 (5) |
| | 0.0025 | 337.3 ± 48.3 * (6) |
| | 0.01 | 553.8 ± 138.3 * (5) |

* p < 0.05 versus carrier (n) = number of rats
s.e.m. = standard error relative to the mean The product of Example 2 is active in this test from a dose of 0.0025 mg/kg.

EXAMPLE 13

Anxiolytic Properties—Ultrasonic Vocalisation Test in the Rat

Principle

When a rat is placed in an environment previously associated with an unpleasant experience (electric shocks to the paws), its anxiety is shown by the emission of inaudible cries (or ultrasonic vocalisations). The anxiolytic activity of a product is demonstrated by a reduction in the duration of those vocalisations.

Apparatus

Standard boxes (Coulbourn Instruments), placed in sound-attenuating ventilated enclosures, are provided with a floor composed of electrifiable metal bars (shock generator and scrambler, Med Associates Inc) and with a microphone located in the centre of the ceiling. The ultrasounds are converted into an audible range (bat detector, Buitenbedrijf). The signals modified in that manner are filtered and then processed (RTS software, Engineering Design). The spectrograms obtained are recorded on DAT tapes.

Method

Male rats of the Wistar strain, weighing 180-200 g on their arrival, are housed in cages of four with free access to food and water, from five days before the start of the study until its end. The procedure employed is divided up into three successive stages separated by 24 hours and called training, selection and test. During the training session, the animals are placed singly in the boxes, where they receive six electric shocks (0.8 mA, 8 s) randomly spaced over a period of seven minutes. Selection comprises placing each animal in a box for two minutes, where they receive a single shock, and putting them back in the box thirty minutes later for a ten-minute session of recording the ultrasonic vocalisations; those animals whose vocalisations last less than 90 seconds are excluded from the remainder of the experiment. The test phase proceeds in a similar manner to the selection stage, with the products or the carrier additionally being administered at the end of the two-minute session. The effect of the products is statistically evaluated by analysis of variance over repeated measurements, followed by a Dunnett's test for comparison of the effects of different doses with the effect of the carrier (distilled water).

Results

By way of example, the following Table shows the effects of the product of Example 2 administered by the s.c. route in a volume of 1 ml/kg.

| Dose Example 2 mg/kg s.c. | Duration of ultrasonic vocalisations (s) mean ± s.e.m. (n) |
|---|---|
| 0 | 254.3 ± 42.1 (7) |
| 0.0025 | 274.0 ± 59.0 (5) |
| 0.04 | 28.0 ± 5.6 * (5) |
| 0.63 | 22.0 ± 3.2 * (5) | s.e.m.: standard error of the mean - n: number of rats
* $p < 0.05$ versus carrier At doses of 0.04 and 0.63 mg/kg, the product causes a substantial reduction in the duration of vocalisations, which indicates its anxiolytic activity.

EXAMPLE 14

Pharmaceutical Composition

| Formula for the preparation of 1000 tablets each containing 10 mg of active ingredient: | |
|---|---|
| Compound of Example 2 | 10 g |
| Hydroxypropylcellulose | 2 g |
| Wheat starch | 10 g |
| Lactose | 100 g |
| Magnesium stearate | 3 g |
| Talc | 3 g |

We claim:

1. A compound selected from those of formula I, which has the trans relative configuration:

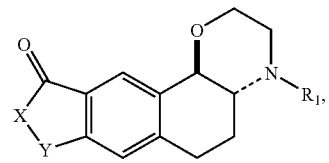

wherein:
X represents an oxygen atom or an $NR_2$ group,
Y represents a group selected from —$CH_2$—, —$(CH_2)_2$— and —CH=CH—,
$R_1$ and $R_2$, which may be the same or different, each represents a hydrogen atom or a group selected from linear or branched $C_1$-$C_6$alkyl, $C_3$-$C_8$cycloalkyl, and $C_3$-$C_8$cycloalkyl $C_1$-$C_6$alkyl wherein the $C_1$-$C_6$alkyl moiety is linear or branched,
in racemic form or in the form of optical isomers,
and addition salts thereof with a pharmaceutically acceptable acid, and hydrates thereof.

2. A compound of claim 1, wherein $R_1$ represents an alkyl group.

3. A compound of claim 1, wherein X represents an $NR_2$ group.

4. A compound of claim 1, wherein Y represents a $CH_2$ group.

5. A compound of claim 1, which is selected from:
(4aRS,11bRS)-4-propyl-3,4,4a,5,6,8,9,11b-octahydroisoindolo[5,6-h][1,4]benzoxazin-10(2H)-one, its enantiomers, and addition salts thereof with a pharmaceutically acceptable acid;
(4aR,11bR)-4-propyl-2,3,4,4a,5,6,8,11b-octahydro-10H-furo[3',4':6,7]naphtho-[1,2-b][1,4]oxazin-10-one, and addition salts thereof with a pharmaceutically acceptable acid;
(4aR,12bR)-4-propyl-3,4,4a,5,6,8,9,12b-octahydro-2H,11H-pyrano[4',3':6,7]naphtho-[1,2-b][1,4]oxazin-11-one, and addition salts thereof with a pharmaceutically acceptable acid;
(4aR,12bR)-4-propyl-2,3,4,4a,5,6,8,9,10,12b-decahydro-11H-isoquino[6,7-h][1,4]-benzoxazin-11-one, and addition salts thereof with a pharmaceutically acceptable acid; and (4aR,12bR)-4-propyl-2,3,4,4a,5,6,10,12b-octahydro-11H-isoquino[6,7-h][1,4]-benzoxazin-11-one, and addition salts thereof with a pharmaceutically acceptable acid.

6. A pharmaceutical composition comprising as active ingredient a compound of claim 1 in combination with one or more inert, non-toxic, pharmaceutically acceptable excipients or carriers.

7. A method of treating a condition selected from Parkinson's disease, hyperprolactinaemia, depression, and anxiety in a living animal body, including a human, comprising the step of administering to the living animal body, including a human, a therapeutically effective amount of a compound of claim 1.

* * * * *